US00PP12201P2

(12) United States Plant Patent
Bedner

(10) Patent No.: US PP12,201 P2
(45) Date of Patent: Nov. 13, 2001

(54) LANTANA PLANT NAMED 'KATIE'

(75) Inventor: Robert Bedner, McDonald, PA (US)

(73) Assignee: Green Leaf Enterprises, Inc., Lancaster, PA (US)

( * ) Notice: Subject to any disclaimer, the term of this patent is extended or adjusted under 35 U.S.C. 154(b) by 0 days.

(21) Appl. No.: 09/624,464

(22) Filed: Jul. 24, 2000

(51) Int. Cl.[7] ..... A01H 5/00
(52) U.S. Cl. ..... Plt./227

(58) Field of Search ..... Plt./227

*Primary Examiner*—Bruce R. Campell
*Assistant Examiner*—June Hwu
(74) *Attorney, Agent, or Firm*—C. A. Whealy

(57) ABSTRACT

A distinct cultivar of Lantana plant named 'Katie', characterized by its outwardly spreading plant habit; freely and continuous branching habit; unique green, light yellow green and light yellow variegated foliage; numerous lavender-colored flowers with white centers; and excellent garden performance and tolerance to high temperatures.

1 Drawing Sheet

BACKGROUND OF THE INVENTION

The present Invention relates to a new and distinct cultivar of Lantana plant, botanically known as *Lantana camara*, and hereinafter referred to by the cultivar name Katie.

The new Lantana was discovered by the Inventor in McDonald, Pa., in April, 1996, as a naturally-occurring branch mutation of an unidentified selection of *Lantana camara*. The new Lantana differs from the mutation parent with its unique green and Light yellow variegated foliage as the parent has solid green-colored foliage.

Asexual reproduction of the new cultivar by terminal cuttings taken in McDonald and Smoketown, Pa. has shown that the unique features of this new Lantana are stable and reproduced true to type in successive generations.

SUMMARY OF THE INVENTION

Plants of the cultivar Katie have not been observed under all possible environmental conditions. The phenotype may vary somewhat with variations in environment such as temperature, light intensity, daylength, and fertility level without, however, any variance in genotype.

The following traits have been repeatedly observed and are determined to be the unique characteristics of 'Katie'. These characteristics in combination distinguish 'Katie' as a new and distinct cultivar:

1. Outwardly spreading plant habit.
2. Freely and continuous branching.
3. Unique green, light yellow green and light yellow variegated foliage.
4. Numerous lavender-colored flower with white centers.
5. Excellent garden performance and tolerance to high temperatures.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photographs may differ slightly from the color values cited in the detailed botanical description which more accurately describe the actual colors of he new Lantana.

The photograph at the top of the sheet comprises a side perspective view of a typical hanging basket plant of 'Katie'.

The photograph at the bottom of the sheet comprises a close-up view of typical flowers and leaves of 'Katie'.

DETAILED BOTANICAL DESCRIPTION

In the following description, color references are made to The Royal Horticultural Society Colour Chart except where general terms of ordinary dictionary significance are used. Plants grown in 11.25-cm containers were planted into 25-cm hanging basket containers about 10–12 weeks and were used for the following description. Plants were grown under outdoor conditions in Keller, Tex. during the spring and summer.

Botanical classification: *Lantana camara* cultivar Katie.

Parentage: Naturally-occurring branch mutation of an unidentified selection of *Lantana camara*, not patented.

Propagation:

*Type cutting.*—Terminal cuttings.

*Time to initiate roots, summer.*—About 4 to 5 days at 29° C.

*Time to initiate roots, winter.*—About 8 to 9 days at 20° C.

*Time to develop roots, summer.*—About 15 to 20 days at 31° C.

*Time to develop roots, winter.*—About 21 to 30 days at 18° C.

*Root description.*—Numerous, fibrous and well-branched.

Plant description:

*Form.*—Perennial flowering plant; subshrub; initially upright, then outwardly spreading; somewhat rounded; rangy. Freely branching; lateral branches potentially forming at every node; pinching enhances lateral branch development.

*Usage.*—Appropriate for hanging baskets, window boxes, patio containers and landscape applications.

*Crop time.*—About 3 to 4 weeks are required to produce finished flowering plants in 11.25-cm containers;

about 10 to 12 weeks are required to produce finished flowering plants in 25-cm containers.

*Plant height.*—About 27 cm.

*Plant diameter.*—About 56 cm.

*Vigor.*—Moderately vigorous.

*Lateral branches.*—Length: About 20 cm. Diameter: About 1 mm. Internode length: About 2.7 cm. Aspect: Initially upright, then bending about 45° from upright. Strength: Flexible, but strong. Texture: Pubescent; fine white hairs; coarse. Color: Brown, 200D to 200C.

*Foliage description.*—Leaves simple, generally symmetrical and long-persisting; opposite. Quantity per lateral branch: About 20. Length: About 3.3 cm. Width: About 2.5 cm. Shape: Ovate. Apex: Acute. Base: Obtuse to truncate. Margin: Crenate. Texture: Rough, coarse; pubescence on both surfaces; rugose. Fragrance: Pungent, herb-like; pleasant. Color: Green, light yellow green and light yellow variegated; variegated patterns random; occasionally leaves may be solid green or solid light yellow. Young foliage, upper surface: Green, darker than 147A to 147B; light yellow green, close to 153D or 154A. Young foliage, lower surface: Green, 147B to close to 143A; light yellow green, close to 154D or 154C. Mature foliage, upper surface: Green, darker than 147A; light yellow, close to 8C to 10D. Mature foliage, lower surface: Green, 147B to close to 147C; light yellow, close to 8C to 10D. Veins, upper surface: 147A to 147B. Veins, lower surface: 147B. Petiole length: About 5.5 mm. Petiole diameter: About 1 mm. Petiole color: 147A.

Flower description:

*Flower type and habit.*—Small salverform flowers arranged in axillary umbels; flowers face mostly upward or outward. Flowers self-cleaning. Very freely flowering with potentially two inflorescences per node; usually upper five nodes develop inflorescences; typically about 20 flowers per umbel.

*Natural flowering season.*—Spring until frost in the autumn; flowering continuous.

*Flower longevity on the plant.*—About one week.

*Fragrance.*—Faint; lilac-like, sweet; pleasant.

*Inflorescence diameter.*—About 3.9 cm.

*Inflorescence height.*—About 1.8 cm.

*Flowers.*—Appearance: Flared trumpet, corolla fused, four-parted; flowers roughly rectangular in shape; iridescent. Diameter: About 1.2 cm by 9 mm. Corolla tube length: About 1.1 cm.

*Flower buds* (*just before showing color*).—Length: About 3.5 mm. Diameter: About 2.5 mm. Shape: Oblong. Color: 146A to 146B.

*Corolla.*—Arrangement/appearance: Single whorl of four petals, fused into flared trumpet. Petal length front throat: Upper petal, about 6 mm; lower and lateral petals, about 4 mm. Petal width: Upper petal, about 7 mm; lower petal, about 6 mm; lateral petals, about 5 mm. Petal shape; Upper and lower petals, somewhat spatulate; lateral petals, mostly orbicular. Petal apex: Rounded. Petal margin: Entire. Petal texture: Smooth, satiny; throat, whiskered. Color: Petal, upper surface, when opening: 80A to 84A; towards base, 155D; throat, bright yellow, 9A, distally; throat, white, 155D, proximally. Petal, lower surface, when opening: 80A to 84A; tube, 80A. Petal, upper surface, fully opened: 84A; throat, white, 155D. Fading to lighter than 84A with development. Petal, lower surface, fully opened: 84A to 84C; tube 80A.

*Sepals.*—Arrangement/appearance: One per flower arranged in a spiral whorl; leaf-like. Calyx length: About 1.3 cm. Calyx width: About 7 mm. Shape: Ovate. Apex: Sharply acute. Margin: Entire. Texture: Pubescent. Color: Upper surface: 146A. Lower surface: 146B.

*Peduncles.*—Length: About 3.2 cm. Diameter: About 1 mm. Angle: About 30° to the stem. Strength: Flexible, but strong. Color: 144A.

*Pedicels.*—Length: Less than 1 mm. Diameter: Less than 1 mm. Color: Close to 144A.

*Reproductive organs.*—Stamens: Quantity: About four. Anther shape: Oblong. Anther length: Less than 1 mm. Anther color: Dark gold. Pollen amount: Scarce, creamy-white in color. Pistils: Quantity: One. Pistil length: Less than 1 mm. Stigma color: Close to 144A. Style color: 144D. Ovary color: 144A.

*Seed.*—Seed production has not been observed.

Disease resistance: Plants of the new Lantana have not been noted to be resistant to pathogens common to Lantana.

Weather tolerance: Plants of the new Lantana have been observed to be tolerant to rain and wind and very tolerant to temperatures about 35° C.

It is claimed:

1. A new and distinct cultivar of Lantana plant named 'Katie', as illustrated and described.

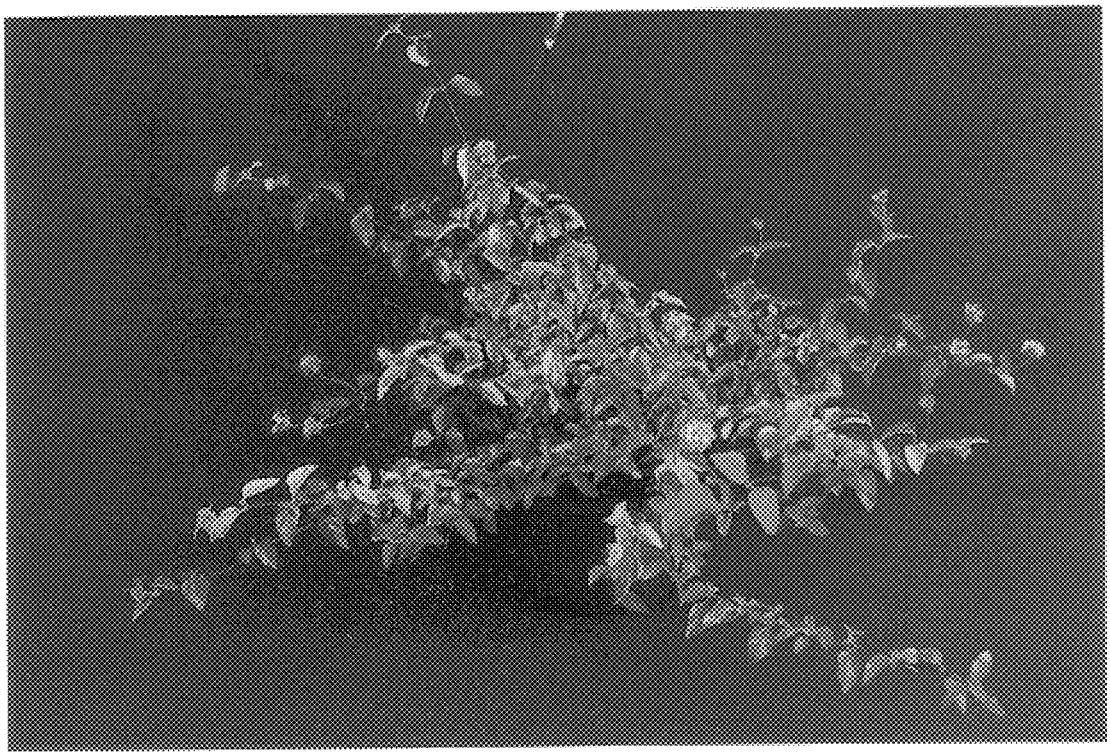
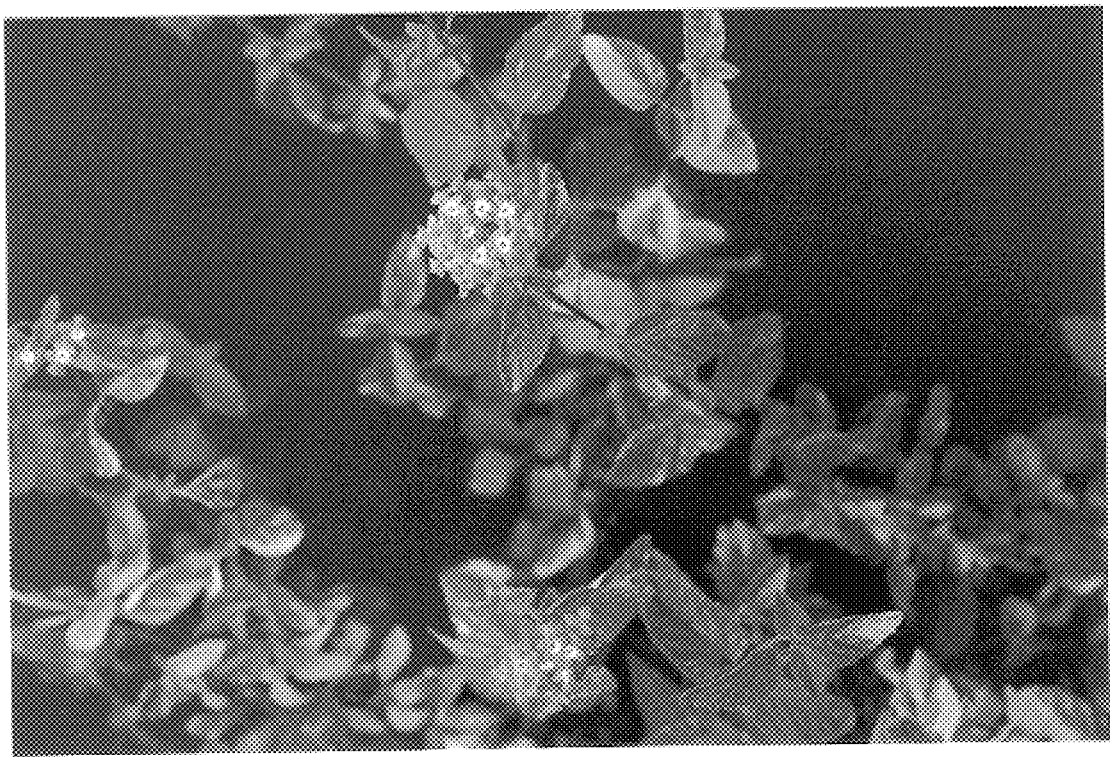

* * * * *